US007527976B2

(12) United States Patent
Hues et al.

(10) Patent No.: US 7,527,976 B2
(45) Date of Patent: May 5, 2009

(54) PROCESSES FOR TESTING A REGION FOR AN ANALYTE AND A PROCESS FOR FORMING AN ELECTRONIC DEVICE

(75) Inventors: Steven M. Hues, Round Rock, TX (US); Hassan F. Fakhreddine, Austin, TX (US); Michael L. Lovejoy, Austin, TX (US); David D. Sieloff, Georgetown, TX (US)

(73) Assignee: Freescale Semiconductor, Inc., Austin, TX (US)

( * ) Notice: Subject to any disclaimer, the term of this patent is extended or adjusted under 35 U.S.C. 154(b) by 790 days.

(21) Appl. No.: 11/060,833

(22) Filed: Feb. 18, 2005

(65) Prior Publication Data

US 2006/0188999 A1 Aug. 24, 2006

(51) Int. Cl.
*G01N 21/62* (2006.01)
(52) U.S. Cl. .................................... 436/171
(58) Field of Classification Search ............. 436/171
See application file for complete search history.

(56) References Cited

U.S. PATENT DOCUMENTS

| | | | | |
|---|---|---|---|---|
| 5,669,979 | A | * | 9/1997 | Elliott et al. .................. 134/1 |
| 5,831,184 | A | | 11/1998 | Willard et al. |
| 6,288,405 | B1 | | 9/2001 | Ng |
| 6,448,097 | B1 | * | 9/2002 | Singh et al. .................. 438/16 |
| 6,610,181 | B1 | * | 8/2003 | Besser et al. ........... 204/192.13 |
| 6,611,577 | B1 | * | 8/2003 | Yamagami .................. 378/48 |

OTHER PUBLICATIONS

C. Streli, et al., "Low Z total Reflection X-Ray Fluorescence Analysis—Challenges Answers," 1999 Elsevier Science B.V., Spectrochimica Acta Part B 54, www.elsevier.nl/locate/sab, pp. 1433-1441, Jan. 8, 1999.

"SEMI M33-0998: Test Method for the Determination of Redidual Surface Contamination on Silicon Wafers by Means of Total Reflection X-Ray Fluorescence Spectroscopy (TXRF)," SEMI 1998, Semiconductor Equipment and Materials International, Mountain View, California, pp. 1-10, 1998.

Sukanta Biswas, et al., "Analytical Techniques for Measuring Contamination Introduced During Ion Implantation," 1997 IEEE, pp. 245-248, 1997.

Poli, V.S. et al.; "SR-TXRF Detection Limit Reduction Using Thin Polymer Film Substrates"; Brazilian Journal of Physics; Sep. 2004; pp. 970-972; vol. 34, No. 3A.

International Search Report and Written Opinion.

Wolf, Stanley, et al. "Silicon Processing for the VLSI Era," Process Technology, vol. 1, Lattice Press, pp. 429-434 and p. 452, 1986.

* cited by examiner

*Primary Examiner*—Walter D Griffin
*Assistant Examiner*—Bobby Ramdhanie

(57) ABSTRACT

A workpiece, including a substrate and overlying layer, can be exposed to a region, such as a process chamber, to test for the presence of an analyte. Detected fluorescence emission signals during TXRD due to the substrate are significantly reduced, allowing the analyte to be detected at lower concentrations. In one embodiment, the substrate can principally include silicon, and the layer can include an organic layer (e.g., resist, polyimide, etc.) The organic layer allows analytes with an atomic number as low as 11 to be detected. Also, the detection limits for nearly all analytes can be reduced because the detector is not receiving a disproportionately larger number of fluorescence emission from silicon. In additional, areal information regarding the analyte with respect to position over the substrate can be obtained. Detection levels as low as 1E9 atoms/cm$^2$ are possible.

10 Claims, 3 Drawing Sheets

US 7,527,976 B2

PROCESSES FOR TESTING A REGION FOR AN ANALYTE AND A PROCESS FOR FORMING AN ELECTRONIC DEVICE

BACKGROUND

1. Field of the Disclosure

The present disclosure relates to processes for testing regions and forming electronic devices, and more particularly to processes for testing a region for an analyte, and optionally, forming an electronic device after testing the region.

2. Description of the Related Art

For x-ray fluorescence spectrometry ("XRF"), when subjected to a primary x-ray flux, analyte atoms on a surface of a silicon substrate absorb the energy of the primary x-ray photon and undergo the process of fluorescence, which results in the emission of a secondary fluorescent x-ray at an energy that is characteristic of the analyte atom. The identity of the analyte atom may be determined by measuring the energy of the fluorescent x-ray photon and the intensity of the photons at that characteristic energy.

In total reflection x-ray fluorescence spectrometry ("TXRF"), the primary x-ray beam strikes a silicon substrate at a very low angle (less than 1°), almost parallel to the surface. At this very low or "grazing" angle, a phenomena termed "total reflection" occurs and the x-ray beam, which would normally penetrate through the entire silicon substrate if the primary x-ray beam would strike the silicon substrate perpendicular to the surface, reflects off the surface, interacting with only the outermost 5 to 10 nm of the substrate surface. A strong fluorescence emission signal is detected due to the presence of the silicon within the substrate. The fluorescence emission signal for silicon is so strong that the ability to detect some analytes is significantly reduced.

In one attempt to solve the problem related to the strong fluorescence emission for silicon includes removing the silicon substrate background fluorescence by depositing liquid samples onto polycarbonate disks for subsequent analysis by TXRF. This suffers for the disadvantage that the tool-level analyte monitors must be subjected to a pretreatment technique, such as a vapor phase decomposition prior to the TXRF analysis. In addition to the added expense and time required for this pretreatment, all areal distribution information concerning the analyte is lost.

BRIEF DESCRIPTION OF THE DRAWINGS

The invention is illustrated by way of example and not limited by the accompanying figures.

Figure 1:
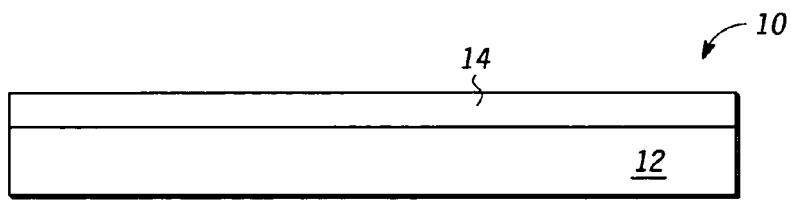
FIG. 1 includes an illustration of a cross-sectional view of a workpiece including a substrate and layer.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

A workpiece can be exposed to a region, such as a process chamber, to test for the presence of an analyte. The workpiece can include a substrate and a layer overlying the substrate. When TXRF is used and the layer is made sufficiently thick, detected signals due to the substrate are significantly reduced, allowing the analyte to be detected at lower concentrations. In one embodiment, the substrate can principally include silicon, and the layer can include an organic layer (e.g., resist, polyimide, etc.) The organic layer allows analytes with an atomic number as low as 11 to be detected. Also, the detection limits for nearly all analytes can be reduced because the detector is not receiving a disproportionately larger number of fluorescence emission from silicon. In additional, areal information regarding the analyte with respect to position over the substrate can be obtained. Detection levels as low as 1E9 atoms/cm$^2$ are possible.

In one aspect, a process for testing a region for analyte includes exposing a workpiece to the region, wherein the workpiece includes a substrate and a layer overlying the substrate, wherein the layer includes a substantially different material compared to the substrate. The method also includes using XRF spectroscopy to analyze the workpiece for an analyte, wherein an x-ray is reflected by the layer during XRF spectroscopy. In one embodiment, the region includes a processing chamber.

In another embodiment, a process for forming an electronic device includes testing the processing chamber for an analyte. Testing is performed by (1) exposing a workpiece to the processing chamber, wherein the workpiece includes a first substrate and a layer overlying the first substrate, wherein the layer includes a substantially different material compared to the first substrate, and (2) using XRF spectroscopy to analyze the workpiece for the analyte. The method also includes determining whether a level of the analyte is no greater than a threshold value, and processing a second substrate within the processing chamber. The second substrate is different from the first substrate and includes an electronic device substrate that includes the electronic device that is at least partially fabricated after processing the second substrate within the processing chamber is completed.

In any of the foregoing embodiment, the processing chamber can be capable of being evacuated to a pressure less than 1 Torr. In other embodiments, the substrate can include an electronic device substrate. In still other embodiments, the layer can include an organic layer. In particular embodiments, the organic layer can include a resist material. In other particular embodiments, the organic layer has a thickness sufficient to substantially prevent excitation of the substrate during using XRF spectroscopy. In still other embodiments, the organic layer has a thickness of at least approximately 300 nm. In further embodiments, XRF spectroscopy can include TXRF spectroscopy. In still further embodiments, the analyte can include an element with an atomic number of at least 11. In yet further embodiments, the analyte can include an element with an atomic number no greater than 18.

Before addressing details of embodiments described below, some terms are defined or clarified. Group numbers corresponding to columns within the Periodic Table of the elements use the "New Notation" convention as seen in the *CRC Handbook of Chemistry and Physics*, 81$^{st}$ Edition (2000).

The term "substantially different" with respect to materials is intended to mean that the composition of one material has a different principal element compared another material. For example, a silicon wafer has silicon as its principal element, and a polymer layer can have carbon and hydrogen as its principal elements. Substantially different is not to be construed to cover a mere surface treatment or exposure to one or more chemicals (e.g., exposure to oxygen or radiation, such as ultraviolet radiation).

The term "substrate" is intended to mean a base material. An example of a substrate includes a quartz plate, a silicon wafer, a silicon-on-insulator wafer, etc. The reference point for a substrate is the beginning point of a process sequence.

The term "workpiece" is intended to mean a substrate at any particular point of a process sequence. Note that the substrate may not significantly change during a process sequence, whereas the workpiece significantly changes during the process sequence. For example, at a beginning of a process sequence, the substrate and workpiece are the same. After a layer is formed over the substrate, the substrate has not changed, but now the workpiece includes the combination of the substrate and the layer.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, for clarity purposes and to give a general sense of the scope of the embodiments described herein, the use of the "a" or "an" are employed to describe one or more articles to which "a" or "an" refers. Therefore, the description should be read to include one or at least one whenever "a" or "an" is used, and the singular also includes the plural unless it is clear that the contrary is meant otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

To the extent not described herein, many details regarding specific materials, processing acts, and circuits are conventional and may be found in textbooks and other sources within the analytical (e.g. x-ray spectroscopic) equipment, semiconductor and microelectronic arts.

FIG. 1 includes an illustration of a cross-sectional view of a workpiece 10. The workpiece 10 includes a substrate 12 and a layer 14. The substrate 12 can be an electronic device substrate, such as a flat panel display substrate or a semiconductor device substrate. A flat panel substrate may be a substrate used in forming a liquid crystal display, a light-emitting diode display, or the like. The semiconductor device substrate may include a monocrystalline semiconductor material, a semiconductor-on-insulator substrate, or any other substrate used in forming semiconductor devices, such as integrated circuits. The semiconductor device substrate can include Si, Ge, C, a III-V semiconductor, a II-VI semiconductor, or any combination thereof. Alternatively, the substrate 12 can include a quartz panel, an aluminum wafer, or the like.

The layer 14 can be formed over the substrate 12 using any one or more conventional deposition techniques. In one embodiment, the layer 14 includes a resist material. The resist material can be positive-acting photoresist, negative-acting photoresist, resist used for radiation outside the visible light spectrum (deep ultra-violet ("DUV") resist), or the like. In one embodiment, the layer 14 includes an organic material, which includes carbon, hydrogen, and any one or more of oxygen, nitrogen, etc. In another embodiment, the layer 14 may include an inorganic insulating or conductive material. The layer 14 can have a thickness that substantially prevents excitation of the substrate 12 during TXRF spectroscopy. The minimum thickness for the layer 14 can be determined empirically by determining a maximum acceptable level of fluorescence emission signal from the material of the substrate 12 (e.g., silicon). When the layer 14 includes an organic material, the thickness can be at least approximately 300 nm. In one specific embodiment, the layer 14 includes a DUV resist and is deposited by a coating the DUV resist material onto the substrate 12 to a thickness in a range of approximately 500 to approximately 1500 nm.

The layer 14 may receive additional processing before the workpiece 10 is used to test a region for an analyte. For example, the layer 14 may be hard baked, be exposed to ultraviolet radiation, receive other post-deposition treatment, or any combination thereof. After reading this specification, skilled artisans will be able to determine a thickness for the layer 14, based at least in part on the material of the layer 14, and potential post-deposition treatment(s) for their particular needs or desires. The workpiece 10 may now be used to test for analyte.

Figure 2:
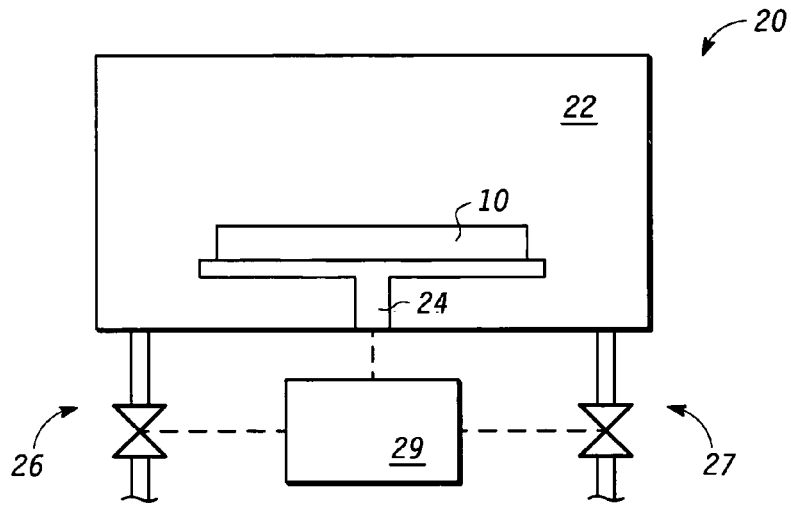
FIG. 2 includes an illustration of a block diagram of a processing tool after the workpiece of FIG. 1 has been placed inside a processing chamber of the processing tool.

Referring to FIG. 2, the workpiece 10 can be placed within a processing tool 20 to analyze the processing chamber 22 for one or more analytes. In one embodiment, the processing tool 20 can be nearly any equipment used in the fabrication of microelectronic devices, and in one specific embodiment, can be a thin-film deposition tool, an ion implant tool, an etch tool, or nearly any other equipment as used within an electronic device fabrication facility. Vacuum processing may be more susceptible to contamination compared to processing at other pressures. For example, an ion implant tool, a physical vapor deposition tool, a chemical vapor deposition tool, or the like may need to be evacuated to a pressure is significantly lower than approximately 1 mTorr, and the process chamber 22 may need to obtain a base pressure of approximately 1E-7 mTorr. In another embodiment, the workpiece can be used to test for an analyte within a room or other location at substantially atmospheric pressure or within a pressurized chamber.

FIG. 2 includes an illustration of a portion of the processing tool 20 and the processing chamber 22 after the workpiece 10 has been placed one a substrate holder 24 within the processing chamber 22. The substrate holder 24 can hold the workpiece 10 in place by use of a vacuum, one or more clamps, electrostatic charge, or any combination thereof. The substrate holder 24 may or may not have a heating element or be capable of movement (e.g., tilting or rotating the workpiece 10). The processing tool 20 includes a gas inlet 26 and a gas outlet 27. Each of the gas inlet and outlet 26 and 27 has an associated valve. The gas inlet 26 may be coupled to one or more gases, such as $N_2$, Ar, one or more conventional etch or implantation gases as used in the microelectronics industry, or any combination thereof. The gas outlet 27 may be connected to a roughing pump, a diffusion or cryogenic pump, a blower, or any combination thereof. Other equipment may be used in conjunction with or in place of the equipment described herein. After reading this specification, skilled artisans will be able to determine the equipment and connections to be used with the processing chamber 22 that meet their particular needs or desires. The substrate holder 24, the valves for one or both of the gas inlet 26 and gas outlet 27, potentially other equipment (not illustrated), or any combination thereof can be controlled by a computer 29 or other controller. The connections between the computer 29 and equipment within the processing tool 20 are illustrated by dashed lines.

The workpiece 10, and more particularly, the layer 14 of workpiece 10 is exposed to a region within the processing chamber 22. The processing tool 20 may be operated in a production (normal) or maintenance mode. For example, for an ion implant tool, a desired dopant may be implanted into the layer 14. An analyte would be anything that adheres to the layer 14 or becomes implanted within the layer 14, other than the desired dopant. In one embodiment, a boron implant ($^{11}B^+$) may be implanted. Phosphorus, which may have been used during a prior operation using the ion implant tool, would be an analyte in this embodiment. A maintenance mode may be merely evacuating the processing chamber 22 (no ion implantation performed). After a predetermined activity (which can include allowing a predetermined amount of time to pass while under vacuum), the workpiece 10 is then removed from the processing tool 20. If the processing chamber 22 was under vacuum, gas can be introduced using the gas inlet 26 to back fill the processing chamber 22, while the valve associated with the gas outlet 27 is closed.

The workpiece 10 including the layer 14, which has been exposed to a potential analyte, can be analyzed using XRF spectroscopy, and more specifically TXRF spectroscopy. In one embodiment, analyses can be performed with a TECHNOS 610T™ brand TXRF instrument available from Technos Company, Limited of Osaka Japan.

Primary x-rays from the TXFR instrument are reflected by the exposed surface of the layer 14. The layer 14 including an organic material, where the organic material may contain atoms having a Z of 9 (fluorine) and lower. In this manner, the layer 14 can be analyzed for analytes, including atoms having Z of 11 (sodium) and higher. In one specific embodiment, analytes having a Z in a range of 11 to 17 may be of particular interest.

As will be described in the examples below, if the layer 14 was not present and the substrate 12 is a nominally bare silicon wafer, a detector used with TXRF spectroscopy could be saturated by fluorescence emission signals from the nominally bare silicon substrate and may not be able to detect elements adjacent to silicon in the Periodic Table, such as aluminum or phosphorus. Therefore, the use of the layer 14 allows a wider range of elements to be examined. Additionally, secondary, tertiary or other fluorescence emission of analyte(s) being analyzed may overlap with the primary fluorescence emission of silicon, or the secondary, tertiary or other fluorescence emission of silicon may overlap with the primary fluorescence emission of analyte(s) being analyzed. The layer 14 effectively reduces the fluorescence emission signal from silicon.

After the workpiece 10 has been analyzed, a determination can be made whether to process product electronic device substrates through the processing tool 20. For example, in an ion implant tool, one or more dopant materials are used to implant species into electronic device substrates. During maintenance, the source region, beam line, or other region within the implant tool may be cleaned to remove unwanted deposits. After the maintenance is completed, the workpiece 10, including the layer 14, is placed into the ion implant tool. The processing chamber 22 is pumped down. In one embodiment, the source region and beam line are not activated (species are not implanted into the layer 14). In another embodiment, a species (e.g., $BF_2$) is implanted into the layer 14. After processing is completed, the layer 14 may be analyzed for residual phosphorus or arsenic within the processing chamber. If phosphorus and arsenic are not present, or are present below at or below predetermined amount, product substrates may be processed.

If phosphorus and arsenic are present above the predetermined amount, the ion implant tool may receive further cleaning or other maintenance. The testing using another workpiece 10, with the layer 14, may be placed in the ion implant tool and tested. The maintenance and testing can be iterated until the phosphorus and arsenic are at or below the predetermined level.

In another embodiment, other equipment may be tested. For example, after a target change, a physical vapor deposition (e.g., evaporation or sputtering) tool may be analyzed for sodium. The workpiece 10, including layer 14, are placed into the processing chamber 22 and exposed to the newly changed target. If sodium is not present, or are present below at or below predetermined amount, product substrates may be processed. Otherwise, further action may be taken with respect to the tool, and testing is repeated.

Figure 3:
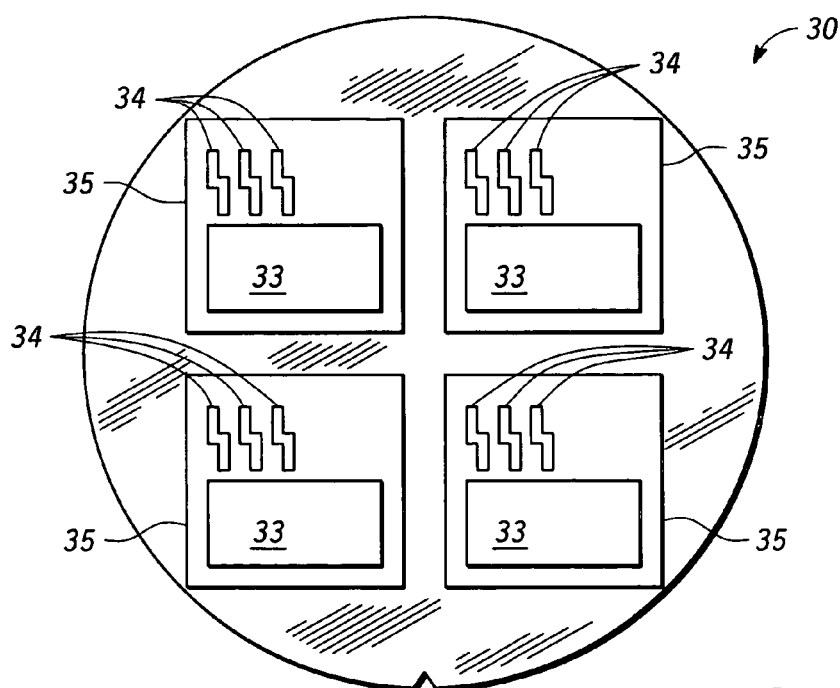
FIG. 3 includes an illustration of a plan view of an electronic device substrate including at least partially fabricated electronic devices.

An electronic device substrate 30 can be processing using the processing tool. The electronic device substrate 30 can be a semiconductor device substrate, as illustrated in FIG. 3. In one embodiment, the electronic device substrate 30 includes partially fabricated electronic devices 35, each of which includes an array 33 of memory cells and circuits 34. In another embodiment (not illustrated), the electronic device substrate may be a flat panel display substrate and have a substantially rectangular shape, instead of a substantially circular shape. The flat panel display may have an array of pixels instead of or in conjunction with an array of memory cells. The electronic device substrate 30 is processed using the processing tool 20.

The electronic device substrate 30 is placed onto the substrate holder 24 similar to workpiece 10 in FIG. 2. The processing operation can depend on the processing tool 20. If the processing tool 20 is an ion implant tool, a dopant can be implanted into the electronic device substrate 30 or a layer overlying the substrate. If the processing tool 20 is a thin-film deposition tool, a thin film is deposited over the substrate. After the process operation is complete, the electronic device substrate 30 is removed from the processing tool. Additional processing of the electronic device substrate 30 may continue to form one or more substantially completed electronic devices.

EXAMPLES

The invention will be further described in the following examples, which does not limit the scope of the invention described in the claims.

Example 1

This example demonstrates that greater sensitivity and relatively lighter elements (Z of no greater than 17) can be detected when using TXRF spectroscopy.

Two tests for analyte are performed within an ion implant tool. One test uses a nominally bare silicon wafer, and the other test uses a workpiece that included a silicon wafer coated with a layer of DUV resist material, similar to workpiece 10 as previously described. Each of the tests is performed using substantially the same conditions within the ion implantation tool. Each of the nominally bare silicon wafer and the workpiece are analyzed using XRF spectroscopy, and more specifically TXRF spectroscopy. The analyses are performed with a TECHNOS 610T™ brand TXRF instrument available from Technos Company, Limited of Osaka Japan.

The TXRF instrument uses a tungsten rotating anode source at approximately 30 KeV and variety of filament current settings in order to produce a series of analyses having increasing primary x-ray fluxes. The instrument is equipped with a curved crystal primary x-ray monochromator having a significantly higher transmission than the standard flat crystal monochromator. In this example, the integration period for the measurements can be approximately 500 seconds.

Figure 4:
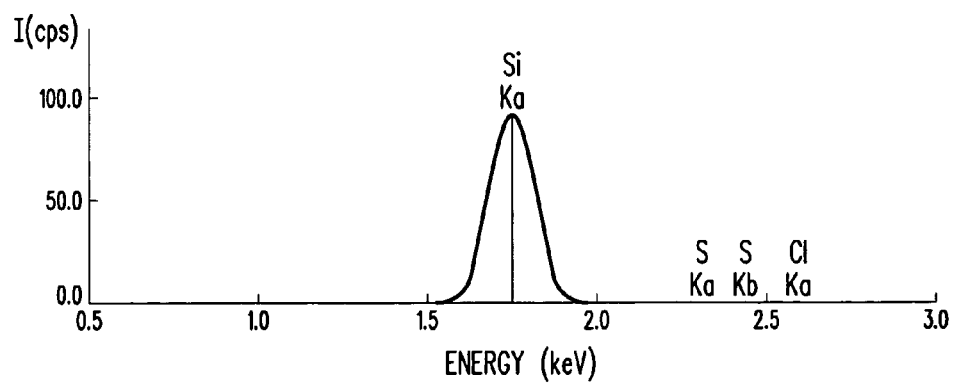
FIG. 4 includes an illustration of an emission spectrum from TXRF spectroscopy when using a nominally bare silicon wafer.

FIG. 4 includes an illustration of the spectrum produced by the nominally bare silicon wafer. The fluorescence emission signal for silicon is so strong that no other elements are detected. The fluorescence emission signals from a nominally bare silicon substrate are so intense that it effectively prevents this instrument from being operated at the maximum filament power level (30 KeV, 200 mA).

Figure 5:
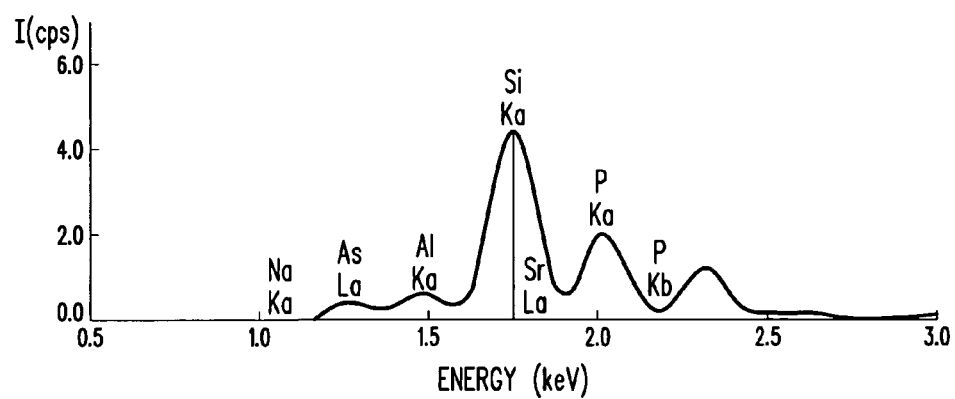
FIG. 5 includes an illustration of an emission spectrum from TXRF spectroscopy when using the workpiece of FIG. 1.

FIG. 5 includes an illustration of the spectrum produced by the workpiece (silicon wafer and layer of DUV resist material). Note that the scale for y-axis in FIG. 5 is different than FIG. 4. The fluorescence emission signal for silicon, at approximately 1.75 KeV, is substantially less in FIG. 5 as compared to FIG. 4. Unlike the nominally bare silicon wafer, the workpiece allows analytes, such as Na, As, Al, Sr, or P to be detected. Table 1 includes data collected regarding detection limits when using the workpiece. The detection limit when using the workpiece is approximately 1.4E11 atoms/$cm^2$.

TABLE 1

| Bragg Scattered W signal (Integrated Counts) | Detection Limit (E10 atoms/$cm^2$) |
| --- | --- |
| 389.70 | 27.7 |
| 499.64 | 25.1 |
| 612.71 | 23.9 |
| 733.39 | 19.2 |
| 850.24 | 19.1 |
| 963.29 | 16.2 |
| 1103.30 | 16.3 |
| 1234.91 | 14.3 |
| 1383.48 | 14.0 |
| 1475.74 | 13.9 |

In addition to greater sensitivity to analytes (lower detection limits), the workpiece can be used to detect elements having Z in a range of 11 to 17, which are elements that are nearly impossible to detect with a nominally bare silicon wafer. Therefore, the workpiece allows the ability to more detect analytes at lower analyte levels and analytes having a lower Z as compared to a nominally bare silicon wafer.

Example 2

Figure 6:
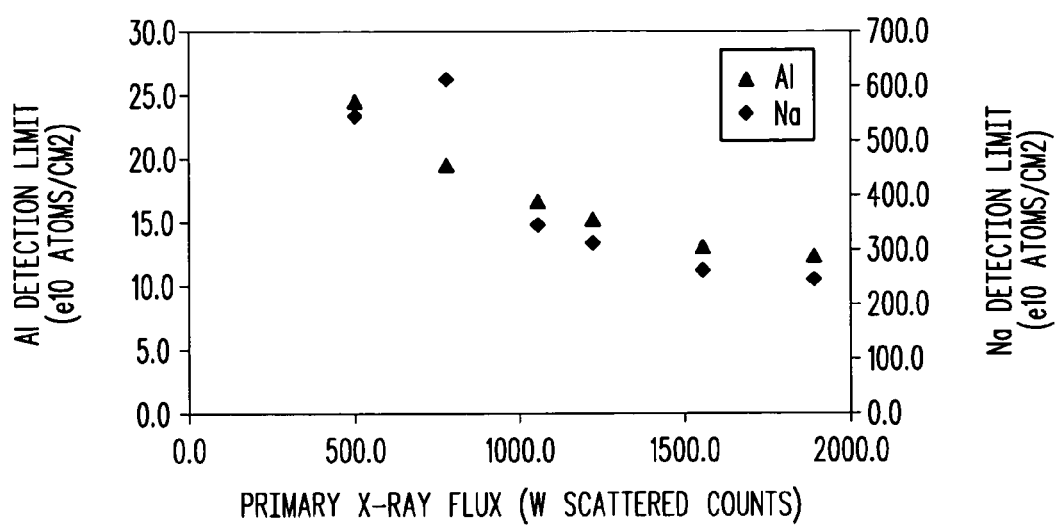
FIG. 6 includes a plot of primary x-ray flux versus analyte concentration illustrating that higher flux can be used and allows for reduced detection limits for sodium and aluminum.

Aluminum and sodium are two analytes that are particularly problematic for microelectronic devices, and particularly, those devices that include metal-insulator-semiconductor field-effect transistors. The workpieces are generated and tested to determine detection limits for aluminum and sodium. Data are presented in FIG. 6 and Table 2 below.

TABLE 2

| W Int Counts | Na | Al |
| --- | --- | --- |
| 487.5 | 552.6 | 24.7 |
| 769.9 | 622.0 | 19.7 |
| 1057.2 | 345.2 | 16.9 |
| 1207.1 | 321.3 | 15.9 |
| 1571.3 | 266.9 | 13.4 |
| 1856.3 | 256.4 | 12.6 |

The data indicate that sodium and aluminum can be detected at levels of approximately 3E12 atoms/$cm^2$ and 2E11 atoms/$cm^2$, respectively. With vapor phase decomposition preconcentration, the detection limits for sodium and aluminum may be reduced by almost two orders of magnitude. The detection limit for sodium can be as low as the low 1E10 atoms/$cm^2$ range, and for aluminum can be as low as the mid 1E9 atoms/$cm^2$ range.

The concepts described herein can be useful for detecting relatively low concentrations of analytes and for detecting elements with Z as low as 11 (sodium). Because the fluorescence signal related to silicon is substantially reduced, the relatively low detection limits can be achieved. Higher x-ray emission rates (as measured by current or primary x-ray counts/second) can be increased when the layer is used to help detect the lower concentrations and elements with atomic numbers. Vapor phase decomposition is not required. Therefore, areal information related to analyte can be retained. The areal information may prove to be very useful in trying to isolate one or more sources of contamination.

Another benefit is that the workpiece can be formed using conventional materials within the microelectronics arts. The substrate used for the workpiece can be the same type of substrate as used for product (e.g., an electronic device substrate). The layer can be formed by coating a resist layer over the substrate and processing it in a manner similar to conventional resist processing as used in forming electronic devices. Therefore, new materials and processes do not need to be developed. Further, the same substrate may be reused multiple times for testing. For example, after a first test, an original resist layer can be removed from a substrate and a new resist layer formed over the same substrate. In an alternative embodiment, the layer may be reused (not removed from the substrate between tests). The sample preparation for testing is relatively straightforward.

Note that not all of the activities described above in the general description or the examples are required, that a portion of a specific activity may not be required, and that one or more further activities may be performed in addition to those described. Still further, the order in which activities are listed are not necessarily the order in which they are performed. After reading this specification, skilled artisans will be capable of determining what activities can be used for their specific needs or desires.

In the foregoing specification, the invention has been described with reference to specific embodiments. However, one of ordinary skill in the art appreciates that one or more modifications or one or more other changes can be made without departing from the scope of the invention as set forth in the claims below. Accordingly, the specification and figures are to be regarded in an illustrative rather than a restrictive sense and any and all such modifications and other changes are intended to be included within the scope of invention.

Any one or more benefits, one or more other advantages, one or more solutions to one or more problems, or any combination thereof have been described above with regard to one or more specific embodiments. However, the benefit(s), advantage(s), solution(s) to problem(s), or any element(s) that may cause any benefit, advantage, or solution to occur or become more pronounced is not to be construed as a critical, required, or essential feature or element of any or all the claims.

What is claimed is:

1. A process for forming an electronic device comprising:
   testing a processing chamber for an analyte by:
      exposing a workpiece to the processing chamber, wherein the workpiece includes a first substrate and an organic layer overlying the first substrate, wherein the organic layer comprises a substantially different material compared to the first substrate; and
      using XRF spectroscopy to analyze the workpiece for the analyte;
   determining whether a concentration level of the analyte is no greater than a threshold value; and
   processing a second substrate within the processing chamber when the concentration level of the analyte is no greater than a threshold value, wherein the second substrate:
      is different from the first substrate; and
      comprises an electronic device substrate that includes the electronic device that is at least partially fabricated after processing the second substrate within the processing chamber is completed.

2. The process of claim 1, wherein the processing chamber is capable of being evacuated to a pressure less than approximately 1 Torr.

3. The process of claim 1, wherein:
   cleaning the processing chamber after determining whether a concentration level of the analyte is no greater than a threshold value and before processing a second substrate within the processing chamber;
   testing the processing chamber another time for the analyte using another workpiece, wherein testing includes using the XRP spectroscopy and is performed after cleaning the processing chamber; and
   determining whether a concentration level of the analyte for the other workpiece is no greater than the threshold value.

4. The process of claim 1, wherein the organic layer comprises a resist material.

5. The process of claim 1, further comprising:
   removing the organic layer from the workpiece after testing the processing chamber;
   forming a resist layer over the first substrate to form another workpiece, wherein forming the resist layer is performed after removing the organic layer;
   testing the processing chamber another time for the analyte, wherein testing includes using the XRF spectroscopy; and
   determining whether a concentration level of the analyte for the other workpiece is no greater than a threshold value.

6. The process of claim 1, wherein the analyte includes an element with an atomic number of at least 11.

7. The process of claim 6, wherein the analyte includes a element with an atomic number no greater than 18.

8. The process of claim 7, wherein the electronic device comprises a metal-insulator-semiconductor field-effect-transistor.

9. The process of claim 8, the organic layer has a thickness sufficient to substantially prevent excitation of the substrate during using the XRF spectroscopy.

10. The process of claim 8, wherein the thickness of the organic layer is at least approximately 300 nm thick.

* * * * *

UNITED STATES PATENT AND TRADEMARK OFFICE
CERTIFICATE OF CORRECTION

| | | |
|---|---|---|
| PATENT NO. | : 7,527,976 B2 | Page 1 of 1 |
| APPLICATION NO. | : 11/060833 | |
| DATED | : May 5, 2009 | |
| INVENTOR(S) | : Steven M. Hues et al. | |

It is certified that error appears in the above-identified patent and that said Letters Patent is hereby corrected as shown below:

Column 10, Line 5, Please change "XRP" to --XRF--.

Column 10, Line 27, Please change "includes a" to --includes an--.

Signed and Sealed this

Eighteenth Day of May, 2010

David J. Kappos
*Director of the United States Patent and Trademark Office*